(12) United States Patent
Suominen

(10) Patent No.: US 8,102,967 B2
(45) Date of Patent: Jan. 24, 2012

(54) GONIOMETER

(75) Inventor: Lasse Suominen, Säynätsalo (FI)

(73) Assignee: Stresstech Oy, Vaajakoski (FI)

( * ) Notice: Subject to any disclaimer, the term of this patent is extended or adjusted under 35 U.S.C. 154(b) by 67 days.

(21) Appl. No.: 12/594,119

(22) PCT Filed: Apr. 3, 2007

(86) PCT No.: PCT/FI2007/050188
§ 371 (c)(1),
(2), (4) Date: Sep. 30, 2009

(87) PCT Pub. No.: WO2008/119868
PCT Pub. Date: Oct. 9, 2008

(65) Prior Publication Data
US 2010/0046708 A1  Feb. 25, 2010

(51) Int. Cl.
G01N 23/20 (2006.01)
(52) U.S. Cl. ........................................................ 378/81
(58) Field of Classification Search .................... 378/70, 378/81, 79, 80, 82, 83
See application file for complete search history.

(56) References Cited

U.S. PATENT DOCUMENTS

| 5,125,016 | A | 6/1992 | Korhonen et al. | |
| 5,148,458 | A | 9/1992 | Ruud | |
| 5,966,423 | A | 10/1999 | Quinn et al. | |
| 6,064,717 | A | 5/2000 | Ortega et al. | |
| 6,408,047 | B1* | 6/2002 | Kitagawa et al. | 378/79 |
| 2003/0012334 | A1* | 1/2003 | Kurtz et al. | 378/73 |
| 2004/0184580 | A1 | 9/2004 | Brauss | |
| 2005/0195942 | A1* | 9/2005 | Brauss | 378/81 |
| 2007/0291899 | A1* | 12/2007 | Suominen | 378/81 |

FOREIGN PATENT DOCUMENTS
WO  WO-2006/056647 A1  6/2006
* cited by examiner

Primary Examiner — Irakli Kiknadze
(74) Attorney, Agent, or Firm — Birch, Stewart, Kolasch & Birch, LLP

(57) ABSTRACT

The invention relates to a goniometer and a method for measuring stresses and characterizing microstructure of particles. The goniometer comprises a base (1), and a measurement head (12) including both an X-ray tube and a detector arc (11) movably adapted to the base (1) by a robot capable for three-dimensional movement. In accordance with the invention the robot has means for creating arc-formed movement of the measurement head (12) during the measurement with rotating (5, 7, 15) and tilting (3, 16, 9) joints.

8 Claims, 5 Drawing Sheets

Fig. 8
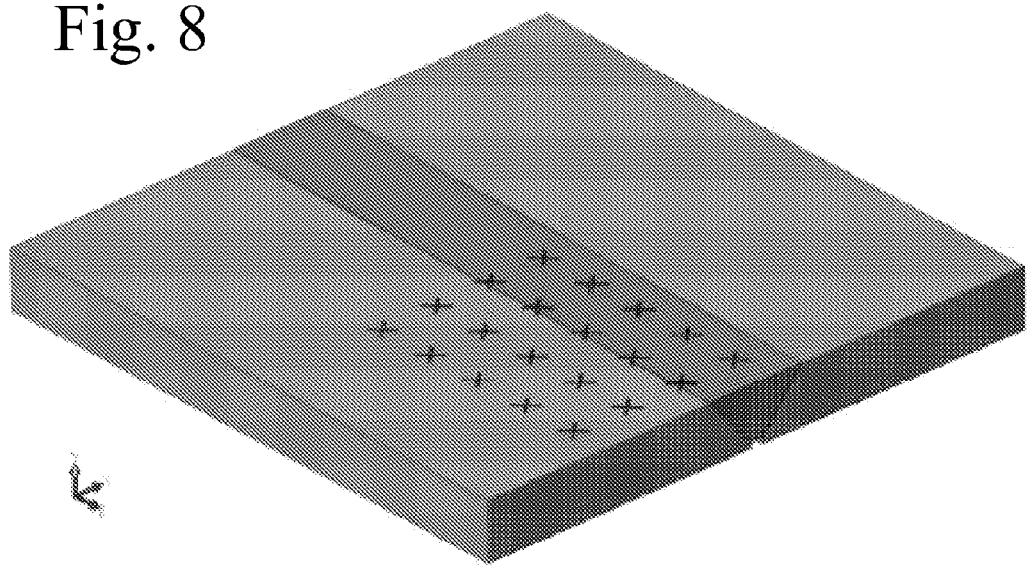
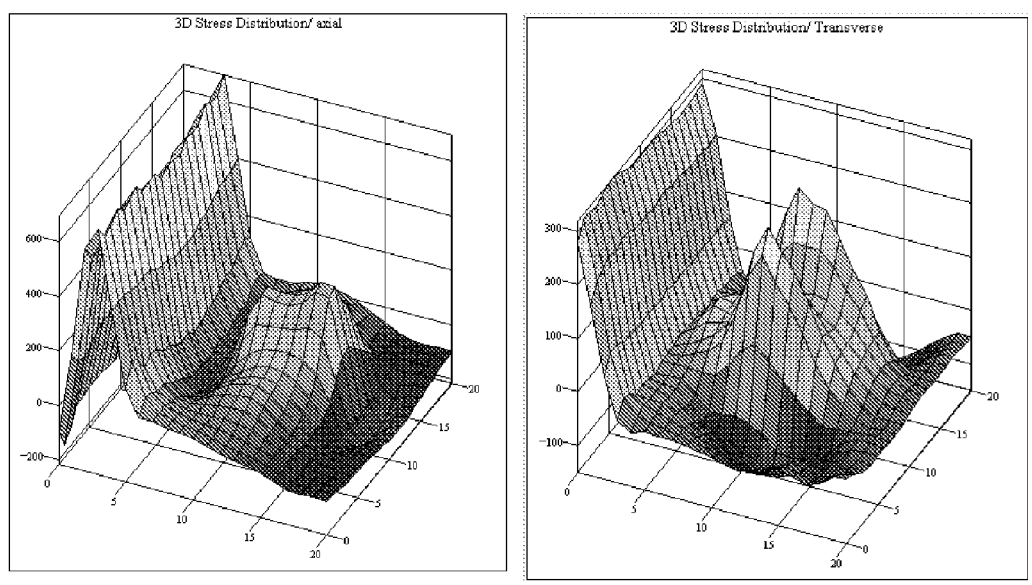
Fig. 9                Fig. 10

GONIOMETER

The present invention relates to a goniometer.

The invention also relates to a method for moving the measurement head of a goniometer.

BACKGROUND OF THE INVENTION

The invention is a movable goniometer or sometimes called diffractometer for measuring stresses and characterizing microstructure. The main purpose of the movability is to be able to measure large and complicated components or structures as crankshafts, gears from few millimeters to meters, bearings, landing gears etc.

The need for control of residual stresses has been intensifying in the recent years almost exponentially, at least if we consider the number of related articles published each year. The main driving force for this expansion is the need to decrease the weight of structures without compromising the safety levels. Residual stresses can have beneficial or detrimental effect on the performance cq. fatigue strength of a component. Typically tensile stresses have a negative effect whereas compressive surface stresses have a positive effect. With this in mind the manufacturing processes such as machining, grinding, welding etc. are designed (optimized) to minimize the residual tensile stresses while in many cases additional treatments are added such as thermal and/or chemical surface hardening, shot peening, burnishing, superfinishing etc. The resulting residuals stress depth-profiles are often strictly prescribed in component quality specifications while parts with different stress values are considered defective. This situation creates a need for fast and reliable quality control. There are numerous methods to measure residual surface stresses. One of most common and time proven is X-ray diffraction by which the lattice plane distances (d), distances between atoms are measured. The compressive stress decreases the lattice distance and correspondingly tensile stress increases it. Specific lattice planes are measured to many directions compared to the surface normal of the measurement point. Due to the stresses on the sample surface the lattice distance changes as the function of the tilt angle. In order to be able to measure lattice planes in different tilt angles, the incident and diffracted beams angle compared to the normal of the measurement surface has to be changed with known amounts. In the laboratory diffractometers this has been done by tilting the sample. In the portable diffractometers respectively the goniometer including X-ray tube and detector(s) is tilted. In the case of position sensitive detector, the detector is fixed together with the X-ray tube, and in the case of a single channel detector system, the detector is moving compared to the X-ray tube.

The two most important factors on residual stress measurement by X-ray diffraction are that the distance between the measurement point and the detector stays constant, (tämä on erikoistapaus) and that the incident beam hits accurately the measurement point in every tilt position. Traditionally this has been done either by a cradle (arc), which is located under the measurement head or with more modern design by linear bearings and rotating tube. This latest solution gives more freedom than the cradle type solution. Stress is vector which has a direction. Tilting of the system has to be done several directions to measure stresses to these directions. Typically in laboratory system the sample is rotated which limits the sample size maximum to few kilograms. Among portable systems there are also rotating goniometers. Both of these solutions are complicated design and difficult to modify which is frequently needed due to complicated sample geometries. Typically also one measurement point is not enough. It is needed to measure distribution for example over weld seam or matrix type of distributions. These are done in the most cases by moving the sample around by x/y tables and in some cases moving goniometer around by x/y table. Again both of these structures are complicated and limits the possible geometries which can be measured.

From U.S. Pat. No. 6,064,717 is known a measurement device with a X-ray tube and detector attached to two different pivoted robot arms. The complicated pivoted arm structures are very difficult to construct accurate enough for X-ray diffraction measurements due to unavoidable backlashes in multiple pivot points. It is very difficult to align correctly; two separate moving arms which has to be aligned compared to each other and also to the measurement point. Even if these problems could be minimized to an acceptable level, the costs would be very high. This solution is not portable or movable.

PCT/FI2005/000505 describes a goniometer implemented by linear movement units. This solution has linear bearings, which limit movements to some extent. The adjustment of the measuring distance is as well rather limited. Rotation of the measurement direction and measurement several points automatically (mapping) has to be arranged additional mechanical devices.

It is an object of the present invention to provide an entirely novel type of goniometer and a control method for a goniomenter.

The present invention is based on using a device in which X-ray tube and detector are positioned in a robot capable for a three dimensional movement and the measurement object is positioned on a immobile base.

In one advantageous embodiment of the invention the robot has means for creating arc-formed movement of the measurement head during the measurement with rotating and tilting joints.

In one advantageous embodiment of the invention the normal of the measurement point is determined automatically by measuring at least three points around the measurement spot. This is done in one advantageous embodiment by touching the surface by the collimator of the goniometer.

In accordance with another advantageous embodiment of the invention the three points are determined by non-contacting measuring methods like ultrasonic or optical measurements. More specifically, the invention is characterized by what is stated in the characterizing portion of Claim 1.

The method according to the invention is characterized by what is stated in the characterizing clause of Claim 5.

The seven most important advantages of this invention are:

1) there is no cradle (arc) or other structures as detectors under the measurement head.
2) No linear bearings (new design) for limiting movements. This means less stumbling with complicated samples.
3) Freely selectable measuring distance by the software.
4) No separate rotation unit, measurement direction determined by software
5) No need for x/y table and it's control unit
6) Commercial available robot substitute many separately built complicated mechanical components.
7) Simple design, for which most of the components can be bought. Simple but very limited structure U.S. Pat. No. 6,064,717 as a performance wise can be avoided. (The complicated, inaccurate and costly structure of U.S. Pat. No. 6,064,717 can be avoided)

In the following, the invention is examined on the basis of an example of an embodiment according to the accompanying drawings.

FIG. 8 shows as a perspective view a welding seam as a measurement target.

FIG. 9 shows measurement results of one measurement.

FIG. 10 shows measurement results of another measurement.

Figure 1:
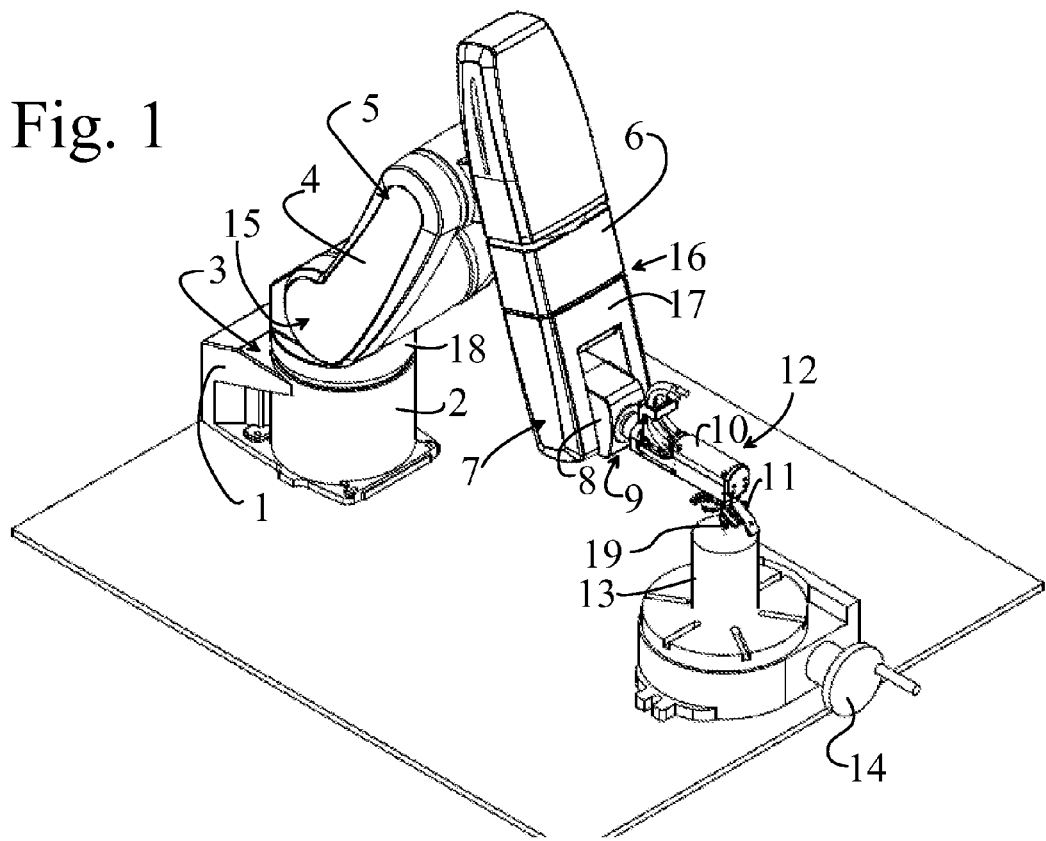
FIG. 1 shows as a perspective view one goniometer in accordance with the invention.

In the following detailed description of the invention the following terms are used:
1 base of the goniometer
2 base element
3 first rotational joint
4 first arm
5 second tilting joint
6 second arm
7 third tilting joint
8 fourth arm
9 third rotational joint
10 X-ray tube housing
11 detector arc
12 measurement head
13 measurement base
14 base adjustment
15 first tilting joint
16 second rotational joint
17 third arm
18 rotating base element
19 collimator
20 plane of the measurement
21 normal of the measurement plane
22 measurement point
23 calibration point According to FIG. 1 the goniometer 1 for measuring stresses includes a robot with six joints, three rotational and three tilting joints. Therefore the X-ray tube housing 10 can be moved freely in three-dimensional space.

In more detail the goniometer includes a base 1 where base element 2 is attached. The base element 2 includes a motor (not shown) for rotating a rotating base element 18 over the first rotational joint 3. First arm 4 is joined to the rotating base element over first tilting joint 15 and correspondingly a second arm 6 is joined to the first arm 4 over second tilting joint 5. Further, the second arm 6 is connected over second rotational joint 16 to a third arm 17. The third arm 17 is connected over third tilting joint to a fourth arm 8, which finally is connected over third rotational joint 9 to the X-ray tube housing 10 forming a measurement head 12. The X-ray tube housing 10 includes an X-ray tube, detector arc 11 and collimator 19. Naturally for three-dimensional movement all of the joints include independently controllable motors.

Figure 2:
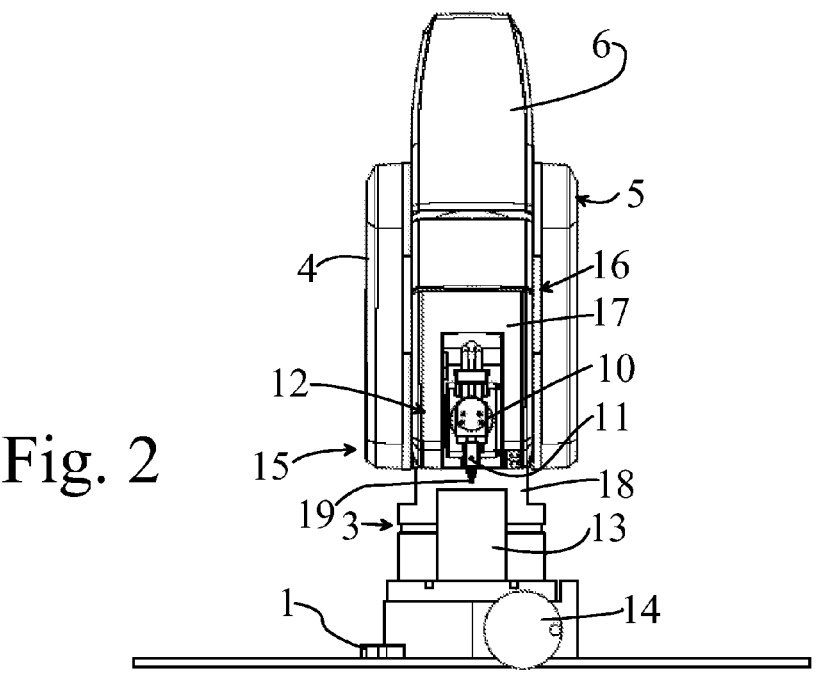
FIG. 2 shows as a front view the goniometer of FIG. 1.

The goniometer in FIGS. 1 and 2 is in a basic position. Measurement base 13 includes an adjustment wheel 14 for adjusting the position of the measuring object. This feature, however is an option, because the goniometer itself is capable to select the measurement by controlling the arms by the joint motors.

Figure 3:
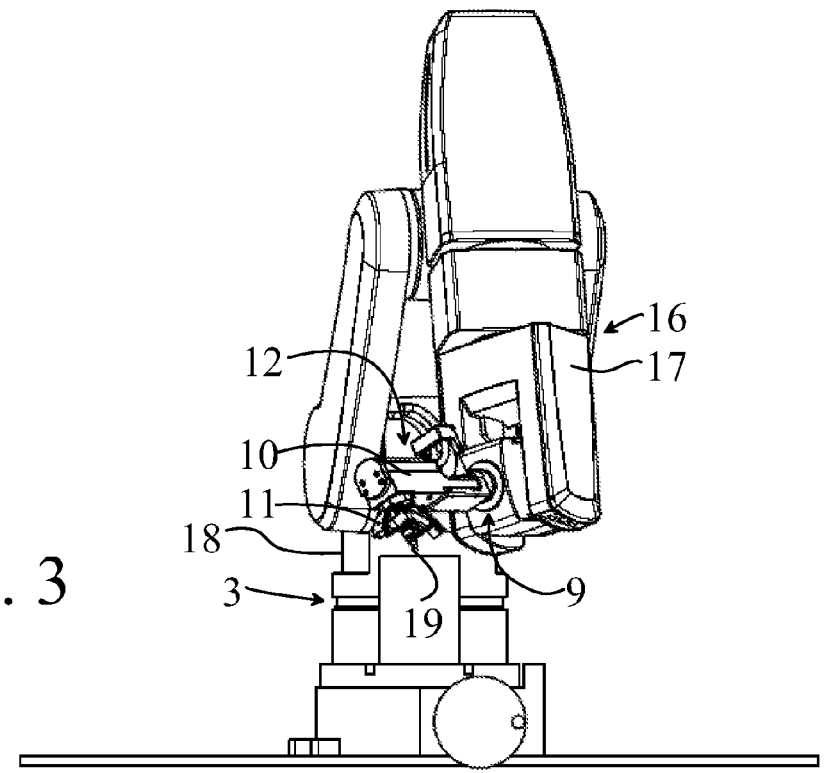
FIG. 3 shows as a front view the goniometer of FIG. 1 in another measuring direction.
Figure 4:
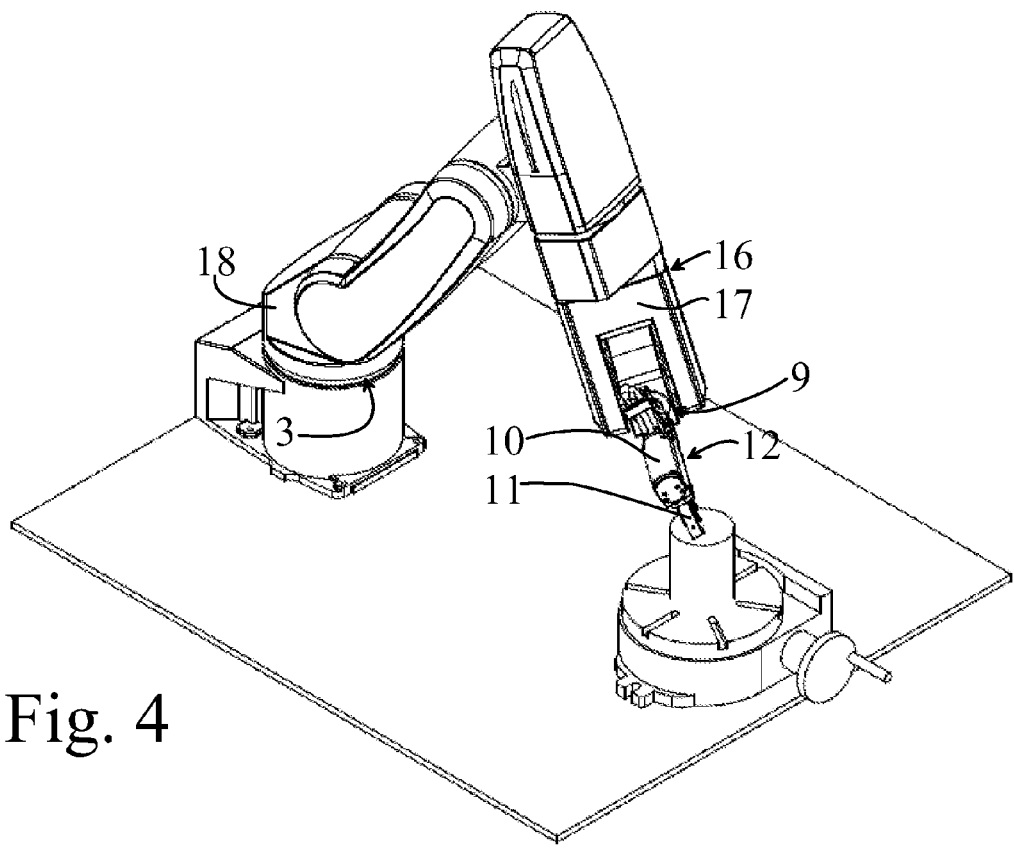
FIG. 4 shows as a perspective view the goniometer of FIG. 3.
Figure 5:
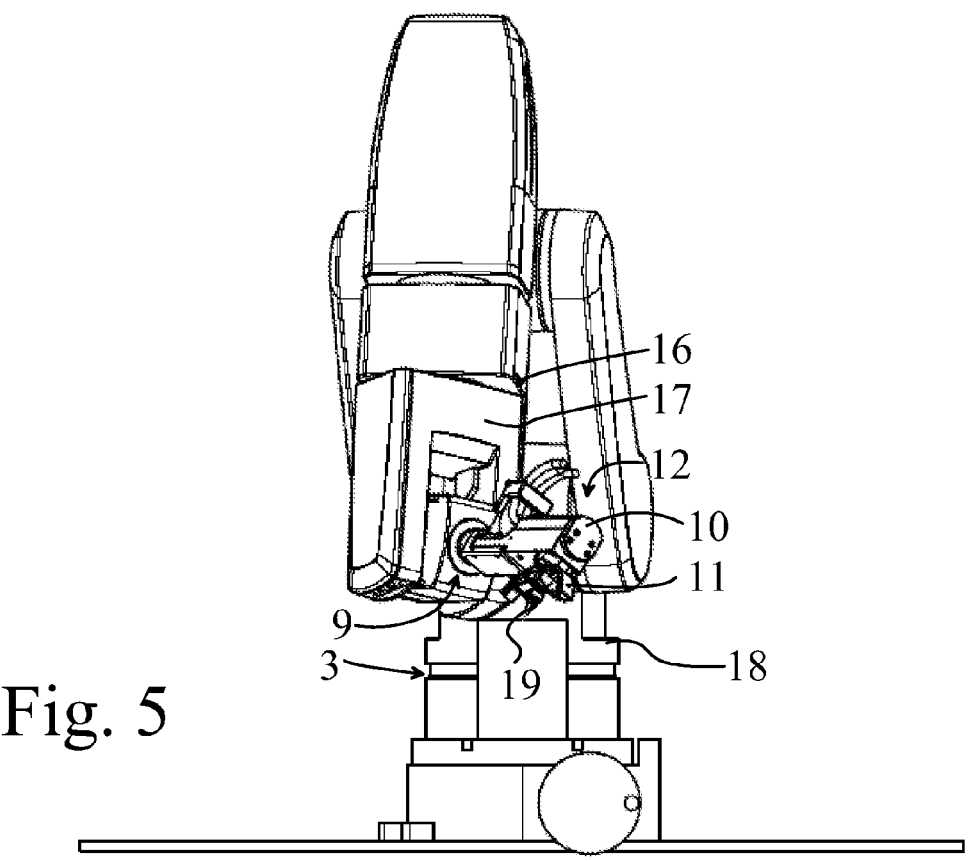
FIG. 5 shows as a front view the goniometer of FIG. 1 in a third measuring direction.
Figure 6:
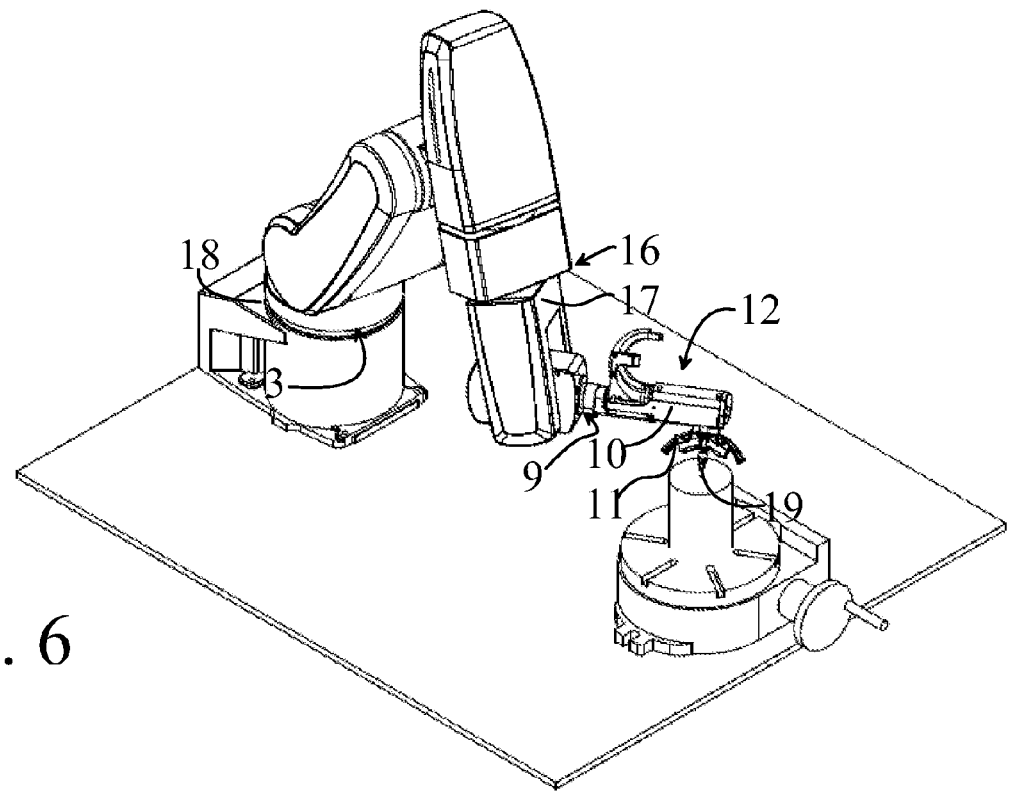
FIG. 6 shows as a perspective view the goniometer of FIG. 5.

In FIGS. 2 and 3 the measurement head 12 is tilted during the measurement in one direction and correspondingly in FIGS. 5 and 6 to another direction.

X-ray tube head 10 with detectors (one or more typically two) are attached to the robot described above. Robot has been programmed to measure one point which is shown manually or by command to it. Robot finds correct distance to measurement point by touching it by collimator or some other method as laser measurement distance system. Robot makes the measurement to the defined direction as axial and repeats the measurement to other directions as circumferential. After this robot can measure next point or points as commanded.

The goniometer in accordance with the invention works so that the measurement head follows precisely the predetermined circular path around the measurement point. The X-ray beam, which is directed to the measurement point through the collimator, hits the correct position always exactly even when moving up and down or horizontally and when tilted.

In addition to the accurate tilting of the measurement head, the accuracy of the distance between the measurement point and the detectors has to be better than 0.05 mm in all tilting positions. The robot movement has to be controlled so that the tube head moves in the circular path all the time. In one important embodiment of the invention the radius of the goniometer can be changed with the software in the range of the robot, and therefore there is no need for additional rotating unit and no need x/y unit.

Also unique for the system is that it finds automatically the normal of the measurement point. This is done by measuring at least three points around the measurement spot. When the relative positions of these points including measurement point are known it can be mathematically found the formula of the surface, which goes through these points and from this formula can be calculated the normal of the measurement point.

Robot goniometer can also include a laser pointer, spring loaded collimator for distance measurement and optional laser distance measurement system. Distance measurements systems are used to find the position of the measurement point as relation to the measurement head. Laser beam is guided through the collimator by mirrors. The goniometer includes also a standard shutter structure and safety features.

Figure 7:
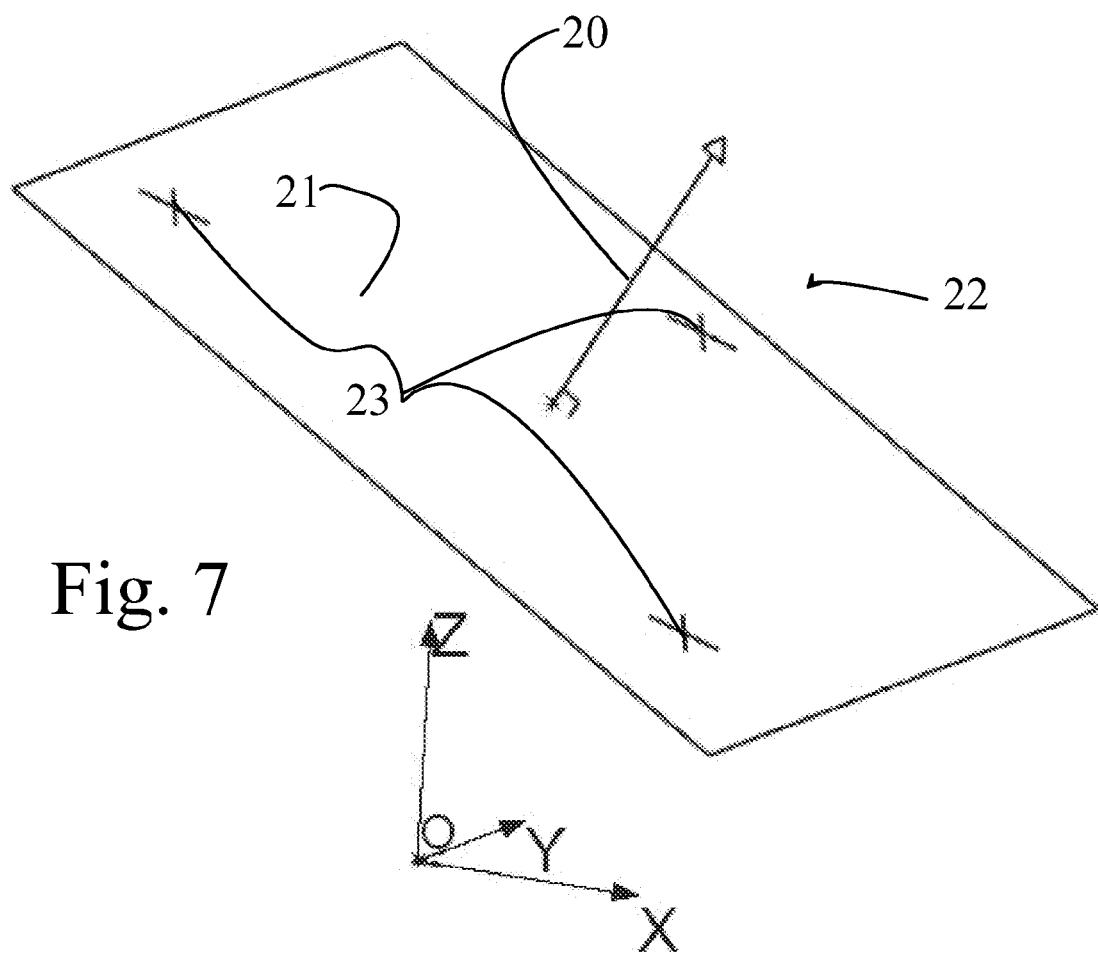
FIG. 7 shows schematically the determination of the normal of the measurement point.

In the following is described with help of FIG. 7 determination the normal direction 20 of the measurement point 22:

At least three calibration points 23 near by the measurement point has been measured by the robot by collimator 19 touch down or another manner. This gives the relative position of the points including the measurement point to the robot coordinate system.

It can be found using linear or nonlinear least square fit method the coefficients of the formula of the plane. This determines the plane, which represents the plane where the measurement point is located.

$$f(x,y,z)=ax+by+cz+d$$

When the plane formula is known the normal 20 of the measurement point 22 can be determined by $$N = \nabla f = \begin{bmatrix} a \\ b \\ c \end{bmatrix},$$

where $\nabla f$ denotes the gradient.

The surface can be other than plane as cylindrical etc.

The goniometer in accordance with the invention works so that the measurement head 12 follows precisely the predetermined circular path around the measurement point 22. The circular path is formed by the robot. The X-ray beam, which is directed to the measurement point 22 through the collimator 19, hits the correct position always exactly even when moving up and down or horizontally and when tilted. In addition, to the accurate tilting of the measurement head 12, the distance between the measurement point and the detectors has to be measured in an accuracy better than 0.05 mm. The movements by all three motors have to be synchronized so that the measurement head 12 moves in the circular path all the time. The synchronization and control are performed either by an internal control unit (not shown) or with an external control unit, which can be a normal tabletop computer equipped with a suitable control program for controlling the motors of each movement unit. Of course, also a combination of internal and external control units may be used for control purposes.

Essential to one embodiment of the invention is that the radius of the goniometer can be freely changed with the software in the range of the robot. Also measurement to different directions without additional rotation unit as also mapping is also one of the advantages of the invention.

The goniometer according to the invention may also include in one preferred embodiment a laser pointer, spring loaded collimator 19 for distance measurement and optional laser distance measurement system.

FIG. 8 shows a typical measurement object, a welding seam and FIGS. 9 and 10 represent correspondingly two measurement results.

The invention claimed is:

1. A goniometer for measuring stresses and characterizing microstructure of particles, comprising
    a base, and
    a measurement head including both an X-ray tube and a detector arc movably adapted to the base by a robot capable of three dimensional movement, wherein
    the robot creating arc-formed movement of the measurement head during the measurement with rotating and tilting joints, and the robot determining a normal of the measurement point by measuring at least three points around the measurement point, determining the normal by touching the surface by a collimator of the goniometer, using a linear or nonlinear least square fit method for finding the coefficients of the formula of a plane representing the plane around the measurement point $$f(x,y,z)=ax+by+cz+d$$

and determining the normal of the measurementpoint by the formula $$N = \nabla f = \begin{bmatrix} a \\ b \\ c \end{bmatrix},$$

where $\nabla f$ denotes the gradient.

2. The goniometer according to claim 1, wherein the robot includes three rotational joints and three tilting joints.

3. The goniometer according to claim 1, wherein independently controllable motors provide the three dimensional movement.

4. The goniometer according to claim 1, wherein the measurement head moves in a circular path and a radius of the goniometer can be changed.

5. A control method for a goniometer for measuring stresses and characterizing microstructure of particles, the method comprising the steps of
    moving a measurement head including both an X-ray tube and a detector arc in a three dimensional space by a robot,
    performing an arc-formed movement of the measurement head during the measurement with the rotating and tilting joints, and
    determining a normal of the measurement point by measuring at least three points around the measurement point, determining the normal by touching the surface of a collimator of the goniometer, using a linear or nonlinear least square fit for finding the coefficients of the formula of a plane representing the plane around the measurement point $$f(x,y,z)=ax+by+cz+d$$

and determining the normal of the measurement point by the formula $$N = \nabla f = \begin{bmatrix} a \\ b \\ c \end{bmatrix},$$

where $\nabla f$ denotes the gradient.

6. The control method for a goniometer according to claim 5, wherein the robot includes three rotational joints and three tilting joints.

7. The control method for a goniometer according to claim 5, wherein independently controllable motors provide the three dimensional movement.

8. The control method for a goniometer according to claim 5, wherein the measurement head moves in a circular path and a radius of the goniometer can be changed.

* * * * *